US005583943A

United States Patent [19]

Ohashi et al.

[11] Patent Number: 5,583,943

[45] Date of Patent: Dec. 10, 1996

[54] ACTIVE NOISE CONTROL SYSTEM WITH DETOURING SOUND APPARATUS

[75] Inventors: Tadashi Ohashi; Tsutomu Hoshino; Atsushi Yamaguchi, all of Kawasaki, Japan

[73] Assignee: Fujitsu Limited, Kawasaki, Japan

[21] Appl. No.: 614,919

[22] Filed: Mar. 11, 1996

Related U.S. Application Data

[63] Continuation of Ser. No. 197,844, Feb. 17, 1994, abandoned.

[30] Foreign Application Priority Data

Feb. 17, 1993 [JP] Japan .................................... 5-027047

[51] Int. Cl.$^{6}$ ............................ A61F 11/06; H03B 29/00

[52] U.S. Cl. ................................................ 381/71; 381/94

[58] Field of Search ......................... 381/71, 94; 415/119

[56] References Cited

U.S. PATENT DOCUMENTS

| | | | |
|---|---|---|---|
| 4,122,303 | 10/1978 | Chaplin et al. . | |
| 4,677,676 | 6/1987 | Eriksson | 381/71 |
| 5,018,202 | 5/1991 | Takahashi | 381/71 |
| 5,146,505 | 9/1992 | Pfaff | 381/71 |

FOREIGN PATENT DOCUMENTS

| | | |
|---|---|---|
| 0615224A2 | 9/1994 | European Pat. Off. . |
| 2636189 | 3/1990 | France . |

*Primary Examiner*—Curtis Kuntz
*Assistant Examiner*—Minsun Oh

[57] ABSTRACT

An active noise elimination apparatus for eliminating noise generated from a blower by generating from a sound generation unit a sound which offsets the noise, in a cooling system for cooling a heat source by air blown from the blower and exhausted to an exhaust port of the system through a duct, includes a first sound reception unit for receiving the noise generated from the blower; a first simulation unit for outputting a sound to the sound generation unit simulating the noise generated from the blower and transmitted to the exhaust port through the duct; a second simulation unit for receiving as input a noise simulating signal of the first simulation unit so as to simulate a detouring sound generated from the sound generation unit and transmitted to the first sound reception unit through the duct; and a subtraction unit for subtracting the detouring sound simulating signal of the second simulation unit from the noise signal received by the first sound reception unit and outputting the result to the first simulation unit.

18 Claims, 9 Drawing Sheets

ACTIVE NOISE CONTROL SYSTEM WITH DETOURING SOUND APPARATUS

This application is a continuation of application Ser. No. 08/197,844, filed Feb. 17, 1994, now abandoned.

BACKGROUND OF THE INVENTION

1. Field of the Invention

The present invention relates to an active noise elimination apparatus, more particularly, an active noise control system with a detouring sound apparatus which precisely eliminates noise by taking into consideration the fact that the sound generated from a sound generation device, for eliminating noise from a noise source, indirectly reaches the noise source.

The environment has become a major social issue in recent years. Noise is also becoming a social issue because it is detrimental to the living and working environments and has an adverse effect on health. Recently, so-called "active noise eliminators" which not only eliminate noise by absorbing it, but also eliminate noise by generating sound waves having the same amplitude, but an opposite phase to the waveforms of the noise, to thereby cancel the noise have attracted increasing attention. There is a strong demand for an active noise eliminator which can be applied to all types of apparatuses and equipments generating noise, such as electrical home appliances and computer systems, and which can eliminate noise efficiently and economically.

2. Description of the Related Art

In a cooling and silencing control system for a large high-speed computer system, which cools the computer system by blowing cool air, cool air is blown from a cooling apparatus below a free-access floor. A cooling control system sucks this cooling air into a duct by a fan and exhausts it through the duct. In this way, the heat generated from heat sources, such as the printed circuit boards of the computer, is guided to and exhausted through the duct. The cooling control system controls the cooling by changing the rotational speed of the fan in accordance with the temperature. In the case of small computers, room temperature air is caused to flow through the heat sources such as the printed circuit boards instead of cool air. In either case, the active noise cancelling controller (ANCC) drives a sound generation device, such as a speaker, based on the noise from the fan (fan noise) received by a sensor microphone, and fan noise received by an error microphone remaining after noise cancellation (residual noise) so as to generate sound waves having the same amplitude but an opposite phase to the fan noise. The fan noise is cancelled out by the sound generated from the speaker (speaker sound) to thus actively eliminate the fan noise.

The fan noise received by the sensor microphone, that is, the microphone disposed in the proximity of the cooling fan (noise source) for cooling the printed circuit boards, etc, is converted from an analog to a digital signal by an analog/digital converter (A/D converter). The signal is then and input to an adaptive type finite impulse response (FIR) filter, giving a transmission coefficient simulating the physical propagation route of the sound through the duct. The output of this FIR filter is converted from a digital to an analog signal by a digital/analog converter (D/A converter). The speaker is driven by this signal so as to generate sound waves having the same amplitude as, but an opposite phase to, the noise generated by the fan. The fan noise is eliminated by being offset by this speaker sound.

The residual noise, which remains when noise cannot be completely eliminated by cancellation of the fan noise by the speaker sound, that is, the sound generated by the error of the result of simulation of the fan noise by the FIR filter (residual error), is received by the error microphone. This analog signal is converted to a digital error signal by the A/D converter. The filter coefficient (or tap coefficient) of the FIR filter is changed on the basis of this error signal so as to bring the residual error, that is, the residual noise, close to zero, and thus completely eliminate the noise generated by the fan.

The processing described above is generally executed within a sampling period t of the A/D converter connected to the sensor microphone and is repeated at intervals equal to the period t to eliminate the fan noise.

The fan noise elimination processing described above is based on the prior art, which does not take into consideration the detouring sound from the speaker to the sensor microphone. In practice, the speaker sound travels indirectly towards the fan, cancels the fan noise, and then is received by the sensor microphone. Accordingly, to efficiently eliminate the noise generated from the cooling system, processing which takes detouring sound into consideration is necessary. Processing for eliminating the influence of the detouring sound is required in the fan noise elimination processing described above.

According to the noise elimination system of the prior art, two FIR filters, that is, an FIR filter for the detouring sound processing and another FIR filter for the fan noise elimination processing, are provided in one processing unit (for example, a digital signal processor: DSP). The detouring sound processing can be executed by the former and then the fan noise elimination processing can be executed by the latter.

However, according to the prior art system described above, since the detouring sound processing and the fan noise elimination processing are executed in series, a long time (for example, about twice the sampling period t of the A/D converter for sampling the noise from the sensor microphone) is necessary for the noise elimination control, and the duct length must be increased (to about double, for example) so as to secure the necessary time. This is economically disadvantageous. To complete the noise elimination processing within the period t without increasing the duct length, a DSP having a higher operating speed and higher performance must be employed. This is neither economical nor efficient.

SUMMARY OF THE INVENTION

It is therefore an object of the present invention to provide an active noise control system with a detouring sound apparatus which can efficiently and economically eliminate noise generated from a noise source and propagating through a duct.

The present invention provides an active noise elimination apparatus in a cooling system for cooling a heat source by air blown from a blower and exhausted to an exhaust port of the system through a duct, that is, an apparatus for eliminating noise generated from the blower by generating, from a sound generation means, a sound which offsets the noise. The apparatus comprises first sound generation means for receiving noise generated from the blower; first simulation means for outputting to the sound generation means a signal for simulating the noise generated from the blower and transmitting to the exhaust port through the duct so as to cancel the noise; second simulation means for receiving an input the noise simulating signal from the first simulation means so as to simulate the detouring sound generated from the sound generation means and transmitted to the first sound reception means through the duct; and subtraction means for subtracting the detouring sound simulating signal of the second simulation means from the noise signal received by the first sound reception means and outputting the result to the first simulation means.

In a cooling system where the duct uses a single suction port of cooling air, the duct is branched into a plurality (N) of branch ducts from an intermediate part thereof, and each of the branch ducts extends to a respective exhaust port through a separate heat source. The active noise control system with the detouring sound apparatus described above further has a plurality (N) of sets of the sound generation means, the first simulation means, and the second simulation means, provided so as to correspond to the plurality (N) of the branch. The subtraction means subtracts a plurality (N) of detouring sound simulating signals of the plurality (N) of the second simulation means from the noise signal received by the first sound reception means and outputs the result to a plurality (N) of the first simulation means.

In a cooling system for cooling a heat source by air blown by a blower and exhausted to an exhaust port of the system through a duct, the present invention further provides an active noise control system with a detouring sound apparatus for eliminating noise generated from the blower by driving a sound generation device disposed in the proximity of the exhaust port to generate a sound which offsets the noise. The apparatus comprises a first sound reception device disposed in the proximity of the blower for receiving the noise; first conversion means for converting an analog signal received by the first sound reception device to a digital noise signal; a first digital filter for outputting a signal simulating the noise generated from the blower and transmitted to the exhaust port through the duct to offset the noise; second conversion means for converting the digital signal from the first digital filter to an analog signal and outputting the analog signal to the sound generation device; a second digital filter for receiving as an input the noise simulating signal of the first digital filter so as to simulate a detouring sound generated from the sound generation device and transmitted to the first sound reception device through the duct; subtraction means for subtracting the detouring sound simulating signal of the second digital filter from the noise signal converted by the first conversion means and outputting the result to the first digital filter; second updating means for receiving as an input the result of the subtraction means to update a filter coefficient of the second digital filter; a second sound reception device disposed in the proximity of the exhaust port of the duct for receiving a residual noise; third conversion means for converting the analog signal from the second sound reception device to a digital residual noise signal; and first updating means for receiving as input the residual noise signal from the third conversion means to update a filter coefficient of the first digital filter.

In a cooling system where the duct uses a single suction port of cooling air, the duct is branched into a plurality (N) of branch ducts from an intermediate part thereof, and each of the branch ducts extends to a respective exhaust port through a separate heat source, the active noise control system of the detouring sound apparatus of the present invention described above further has a plurality (N) of sets of the first digital filter, the second conversion means, the sound generation device, the second sound reception device, the third conversion means, the first updating means, the second digital filter, and the second updating means, provided so as to correspond to the plurality (N) of the branch ducts, wherein the subtraction means subtracts a plurality (N) of detouring sound simulating signals of the plurality (N) of the second digital filters from the noise signal converted by the first conversion means and outputs the result to the plurality (N) of the first digital filters.

According to the present invention, the first simulation means, and second simulation means, and also the first digital filter and second digital filter of each of the sets described above, are constituted by separate processing units. The two processing units communicate by directly issuing an interrupt to the counterpart processing unit, by indirectly issuing an interrupt through another processing unit disposed between the two, by giving information through an interface disposed between the two processing units, or by monitoring every predetermined time that existing data is to be exchanged with the counterpart processing unit.

BRIEF DESCRIPTION OF THE DRAWINGS

The present invention will be more clearly understood from the description as set forth below with reference to the accompanying drawings, in which.

DESCRIPTION OF THE PREFERRED EMBODIMENTS

Before describing the preferred embodiments according to the present invention, examples of the related art will be given with reference to FIGS. 1 to 3.

Figure 1:
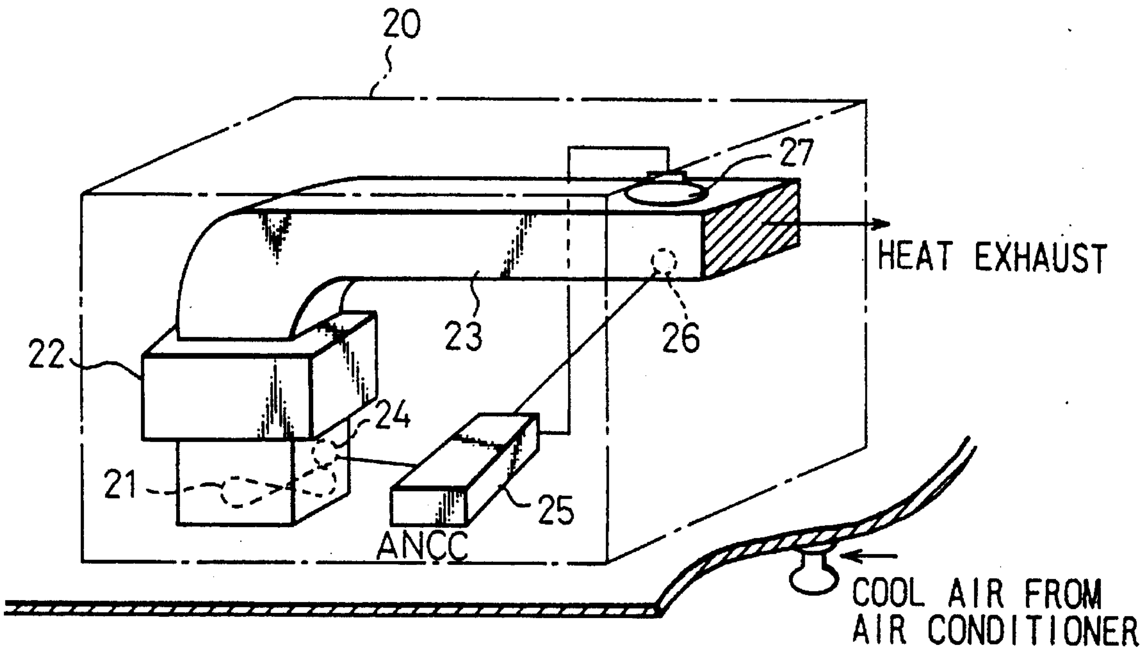
FIG. 1 is an explanatory view of a cooling and silencing control system of a computer system.

FIG. 1 is an explanatory view of a cooling and silencing control system of a computer system and shows particularly a silencing control system of a large high-speed computer system which is cooled by cool air.

Cool air is blown from a cooling apparatus under a free access floor. A cooling control system sucks cool air into a duct 23 by a fan 21 and exhausts it through the duct 23. In this way, heat which is generated from heat sources 22, such as printed circuit boards of a computer, and guided to the duct 23 is exhausted through the duct 23 to cool the computer. In this instance, the cooling control system controls the cooling by changing the speed of the fan 21 etc. in accordance with the temperature. A small computer is cooled by causing room temperature air to flow through the heat sources 22 instead of cool air. In either case, the ANCC 25 actively eliminates noise from the fan 21 (fan noise), received by a sensor microphone 24, by driving a sound generation device 27 such as a speaker, on the basis of the fan noise and a fan sound (received by an error microphone 26 and after silencing), to generate a sound wave having the same amplitude as, but an opposite phase to, the fan noise. The fan noise and sound generated from the speaker (speaker sound) are thus offset from each other to cancel the fan noise.

Figure 2:
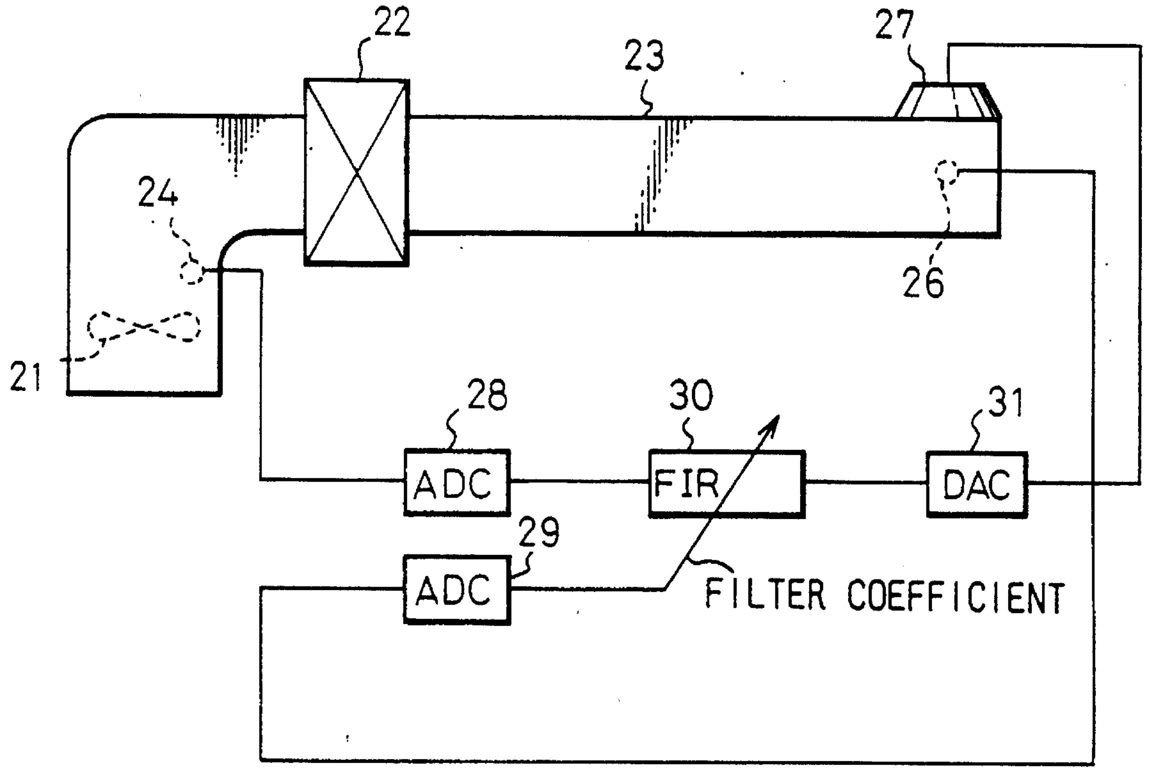
Fig. 2 (PRIOR ART)
FIG. 2 is a block diagram of a silencing control as an example of the prior art.

FIG. 2 is a block diagram of a silencing control system according to the related art.

A microphone (sensor microphone 24) disposed in the vicinity of the cooling fan 21 (noise source), for the printed circuit boards etc, receives the fan noise. This fan noise is converted from an analog sound signal to a digital signal by an A/D converter 28, and is input to an FIR filter 30 which gives a transmission function simulating a physical propagation route of the sound by the duct. The output of this FIR filter 30 is converted from a digital to an analog signal by a D/A converter 31. The speaker 27 is driven by this analog signal so as to generate a sound wave having the same amplitude as, but an opposite phase to, the noise generated by the fan 21. The speaker sound offsets the actual fan noise with the simulated fan noise.

The residual noise which remains when the noise is not completely eliminated by the offset of the speaker sound and the fan noise, that is, the sound which is generated due to the error (residual error) of the result of simulation of the fan noise by the FIR filter 30, is received by the error microphone 26. Its analog sound signal is converted to a digital error signal by the A/D converter 29. The filter coefficient (or tap coefficient) of the FIR filter 30 is changed on the basis of this error signal so as to bring the residual error, that is, the residual noise, close to zero, so as to completely eliminate the noise generated by the fan.

The processing described above is executed within a sampling period t of the A/D converter 28 connected to the sensor microphone 24 and is repeated at intervals of the period t to eliminate the fan noise.

However, the fan noise elimination processing described above does not take the detouring sound from the speaker 27 to the sensor microphone 24 into consideration. In practice, the speaker sound advances indirectly towards the fan, cancels the fan noise, and then is received by the sensor microphone 24. Accordingly, in order to efficiently eliminate the noise generated from the cooling system, processing which takes the detouring sound into consideration becomes necessary. Processing for eliminating the influences of the detouring sound becomes necessary, as well, during the fan noise elimination processing described above.

Figure 3:
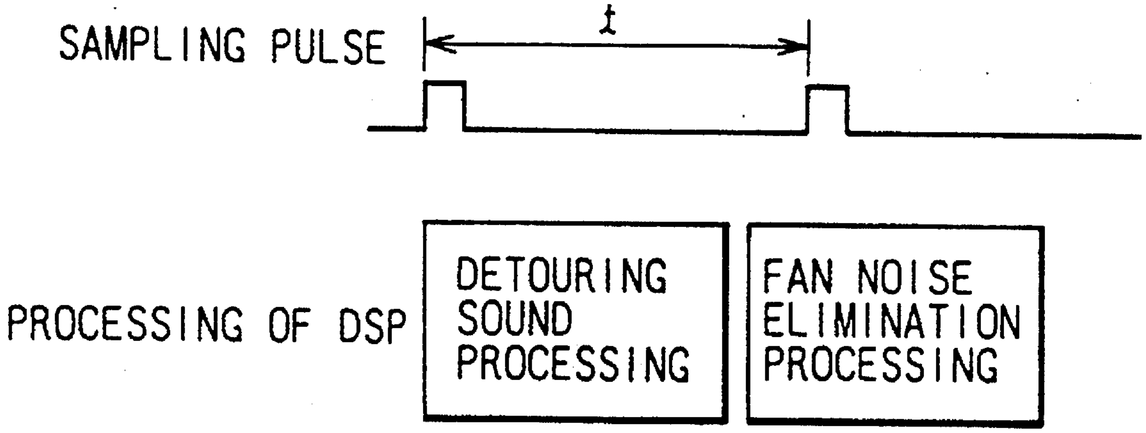
Fig. 3 (PRIOR ART)
FIG. 3 is an explanatory view of a noise elimination system according to the prior art.

FIG. 3 shows the noise elimination system according to the related art.

As shown in the figure, the conventional system is provided with two FIR filters, one for the detouring sound processing and one for the fan noise elimination processing. One processor (such as a DSP), executes first the detouring sound processing by the former, and then executes the fan noise elimination control by the latter.

According to the related art system described above, the detouring sound processing and the fan noise elimination processing are executed in series. Accordingly, a long time (for example, a time about twice the sampling period t of the A/D converter of the noise from the sensor microphone) is required for the noise elimination control. This results in an economical disadvantage because the duct must be extended in length (for example, about double) so as to compensate for the necessary time. To complete the noise elimination processing within the period t without extending the duct length, a DSP having a higher processing speed and higher performance must be used. This is neither economical nor efficient.

Figure 4:
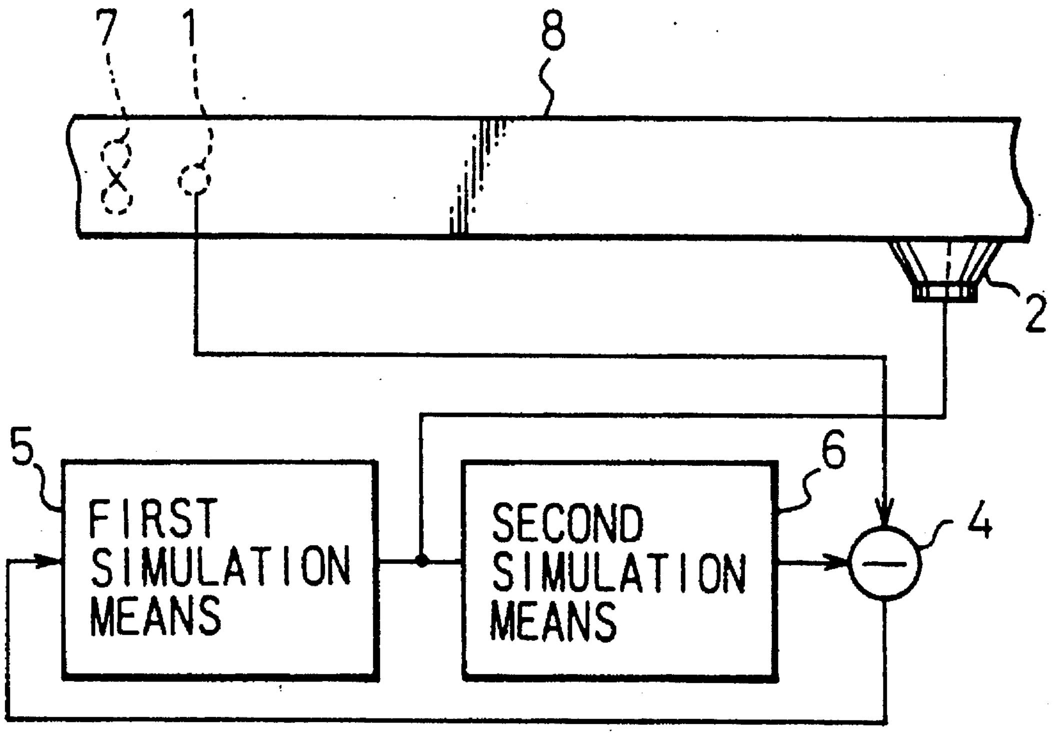
FIG. 4 is a block diagram for explaining the principle of the present invention.

Next, FIG. 4 is a block diagram for explaining the principle of the present invention.

FIG. 4 shows a cooling system wherein air is sent from the blower 7 to the exhaust port through the duct 8 to cool the heat sources. The present invention provides an active noise elimination apparatus for eliminating the noise generated from the blower 7 by generating a sound offsetting the noise by the sound generation means 2. The first simulation means 5 sends a signal (to offset the noise) to the sound generation means 2, simulating the noise generated from the blower 7 and transmitted to the exhaust port through the duct 8, the second simulation means 6 receives the noise simulating signal of the first simulation means 5 and simulates the detouring sound generated from the sound generation means 2 and transmitted to the first sound reception means 1 through the duct 8. The subtraction means 4 subtracts the detouring sound simulating signal of the second simulation means 6 from the noise signal received by the first sound reception means 1. The first simulation means 5 executes simulation on the basis of the result of the subtraction. Therefore, the present invention can simulate the noise generated from the blower 7 free of the detouring sound.

Figure 5:
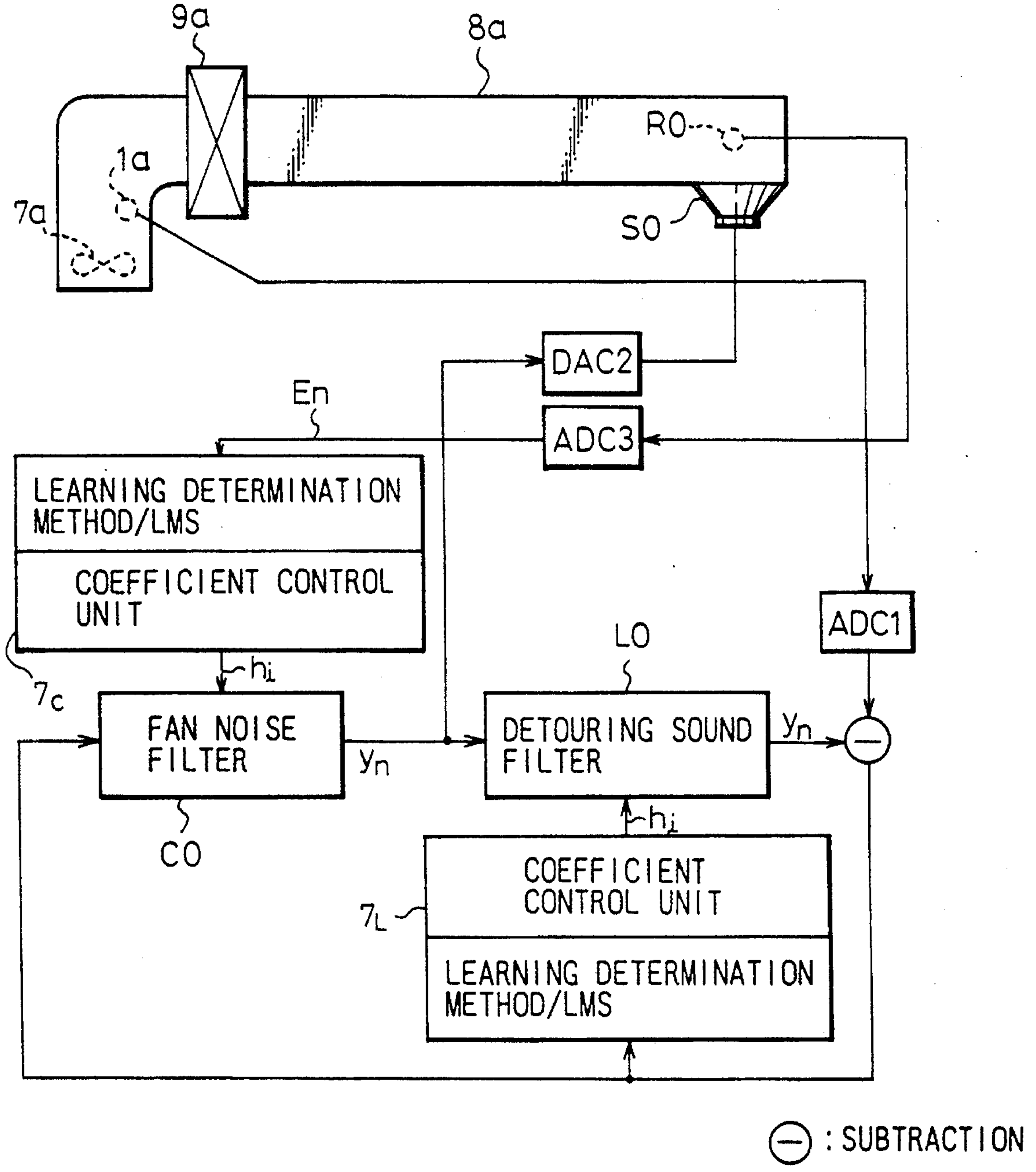
FIG. 5 is a block diagram showing a first embodiment of the present invention.

FIG. 5 is a block diagram showing the first embodiment of the present invention. Note that the same reference numerals will be used to identify similar constituent elements throughout all the drawings.

An adaptive FIR filter CO and filter LO are provided for fan noise processing and detouring sound processing. These are disposed in two separate processors (for example, digital signal processors) DSPC and DSPL, respectively. The fan noise filter CO simulates the behavior of the fan noise transmitted from the fan 7a to the exhaust port through the duct 8a by a transmission function. The detouring sound filter LO simulates the behavior of the speaker sound traveling from the speaker SO to the sensor microphone 1a through the duct 8a by a transmission function.

Figure 6:
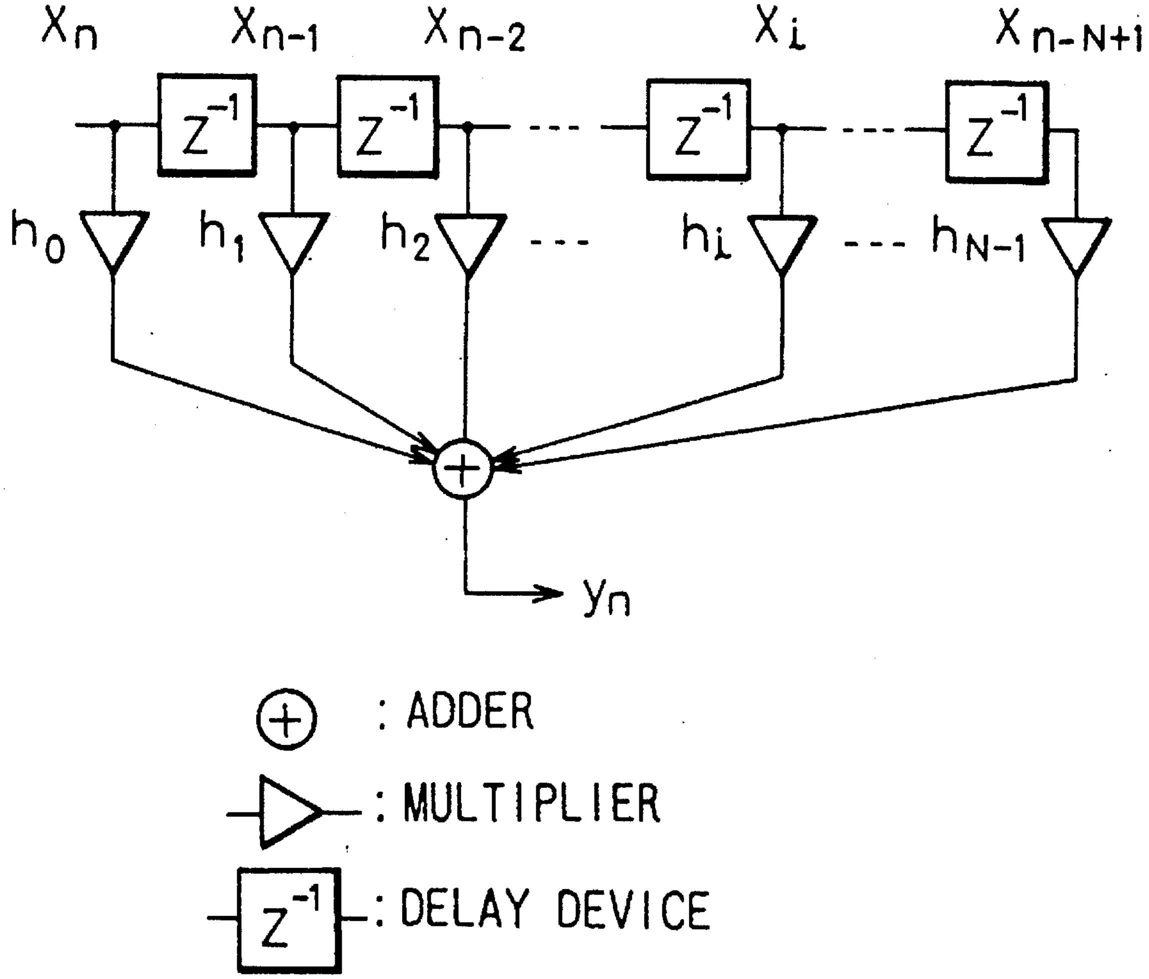
FIG. 6 is a structural view of an FIR filter.

FIG. 6 is a structural view of the FIR filter, it shows an example of a fan noise filter CO and detouring sound filter LO of N stages (or N taps) comprising a delay device, a multiplier, and an adder.

An output $y_n$ at a time n is given by the following convolution computation;

$$y_n = \sum_{i=0}^{N-1} h_i \cdot x_{n-1}$$

where $\{x_i\}$ and $\{y_i\}$ are signal series of the input/output of the FIR filters which are dispersive on the time axis, and $h_i$ is a filter coefficient, which is automatically updated by later-appearing coefficient control units 7C and 7L in a manner so as to minimize the error of the output $y_n$ of the simulation result.

Turning back again to FIG. 5, the noise received by the sensor microphone 1a (disposed in the vicinity of the fan 7a for cooling the heat source 9a such as a printed circuit board), and i.e. generating noise (the combined sound of the fan noise and the speaker sound) is converted from an analog signal to a digital signal by the A/D converter ADC1.

The output $y_n$ of the fan noise filter CO drives the speaker SO through the D/A converter DAC2 to eliminate the fan noise and is also input to the detouring sound filter LO. Since the detouring sound filter LO simulates the speaker sound traveling to the sensor microphone 1*a*, the difference signal obtained by subtracting the output $y_n$ of the detouring sound filter LO from the output of the A/D converter ADC1 represents the pure fan noise from which the detouring sound component is removed. This difference is input to the fan noise filter CO and to the coefficient control unit 7L. The coefficient control unit 7L corrects the filter coefficient $h_1$ ($h_0, h_1, h_2, \ldots$) of the detouring sound filter LO on the basis of the input difference, updates the filter coefficient, and controls the system to minimize the simulation error of the detouring sound filter LO.

The fan noise filter CO simulates the fan noise transmitted to the exhaust port through the duct 8*a* by inputting the difference described above representing the pure fan noise. The output $y_n$ of the fan noise filter CO is converted from a digital to an analog signal by the D/A converter DAC2. The speaker SO is driven by this signal so as to generate a sound wave having the same amplitude as, but an opposite phase to, the noise generated by the fan 7*a*. In this way, the speaker sound and the fan noise are offset with each other so as to eliminate the fan noise.

The sound which remains due to incomplete elimination of the fan noise, that is, the residual noise resulting from the error of simulation of the fan noise by the fan noise filter, is received by the error microphone RO and is converted to a digital signal by the A/D converter ADC3. This digital signal is input as the residual error En to the coefficient control unit 7C. The coefficient control unit 7C corrects and updates the filter coefficient $h_1$ ($h_0, h_1, h_2, \ldots$) of the fan noise filter CO on the basis of the input residual error En and brings the residual error, that is, the residual noise, close to zero, to completely eliminate the noise generated by the fan 7*a*.

Next, an example of the method of determining the filter coefficient will be explained.

Figure 7:
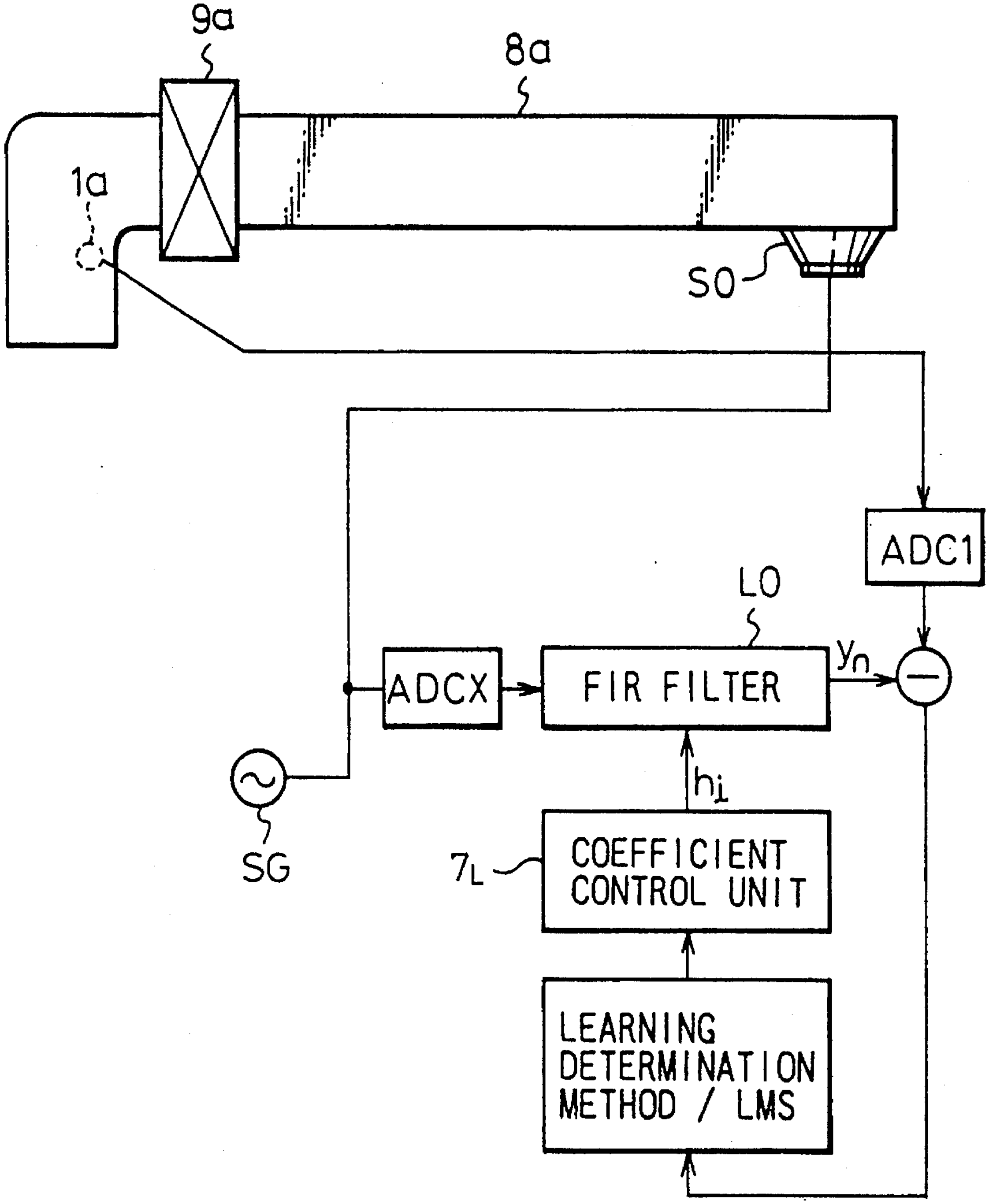
FIG. 7 is a view for determining a filter coefficient of a filter for detouring noise.

FIG. 7 is a view for explaining the method of determining the filter coefficient of the detouring sound filter.

The fan 7*a* is stopped, and a pseudo-sound generator SG generates a false detouring sound. The output of this pseudo-sound generator SG is used to drive the speaker SO and is input to the detouring sound filter LO through the A/D converter ADCX. The sound generated from the speaker SO travels inside the duct 8*a* and is received by the sensor microphone 1*a*. It then passes through the A/D converter ADC1 and is converted to a digital detouring sound signal. The output $y_n$ of the detouring sound filter LO is subtracted from this detouring sound signal, and the transmission function of the impulse response is estimated by a learning determination method or a least mean square (LMS) method to obtain a filter coefficient $h_1$ which makes the result of subtraction zero. The procedures described above are repeated while changing the output of the pseudo-sound generator SG, so the filter coefficient $h_1$ corresponding to the change of the output value is learned.

Next, the connection is returned to the one shown in FIG. 5, and the detouring sound filter LO and the fan noise filter CO are then operated. In this case, the sound is generated from the pseudo-sound generator SG disposed in the proximity of the fan 7*a*, and the detouring sound filter LO is operated on the basis of the filter coefficient $h_i$ obtained by learning described above. Due to the result of learning described above, the detouring sound filter LO correctly simulates the detouring sound. As a consequence, the result of subtraction represents the pure fan noise devoid of the detouring sound. In this way, the transmission function of the impulse response is estimated by the learning determination method or by the LMS method so as to obtain the filter coefficient $h_i$ which makes the output of the error microphone RO zero. The procedures described above are repeated by changing the output of the pseudo-sound generator SG, so the filter coefficient $h_i$ corresponding to the change of the output value is learnt.

The explanation given above is of the example wherein the filter coefficient $h_i$ of the fan noise filter CO is determined only on the basis of the output of the error microphone RO, but the temperature of the heat source 9*a* may be added as one of the factors for determining the filter coefficient $h_i$. In other words, in the cooling system, the temperature of the heat source 9*a* is generally measured, and control is performed so that the temperature of the heat source 9*a* quickly falls within a desired temperature range. The speed of the fan 7*a* is changed on the basis of the temperature thus measured, that is, on the basis of proportional, integration and differential (PID) values of the temperature change, for example. Accordingly, the noise can be eliminated more efficiently.

Figure 8:
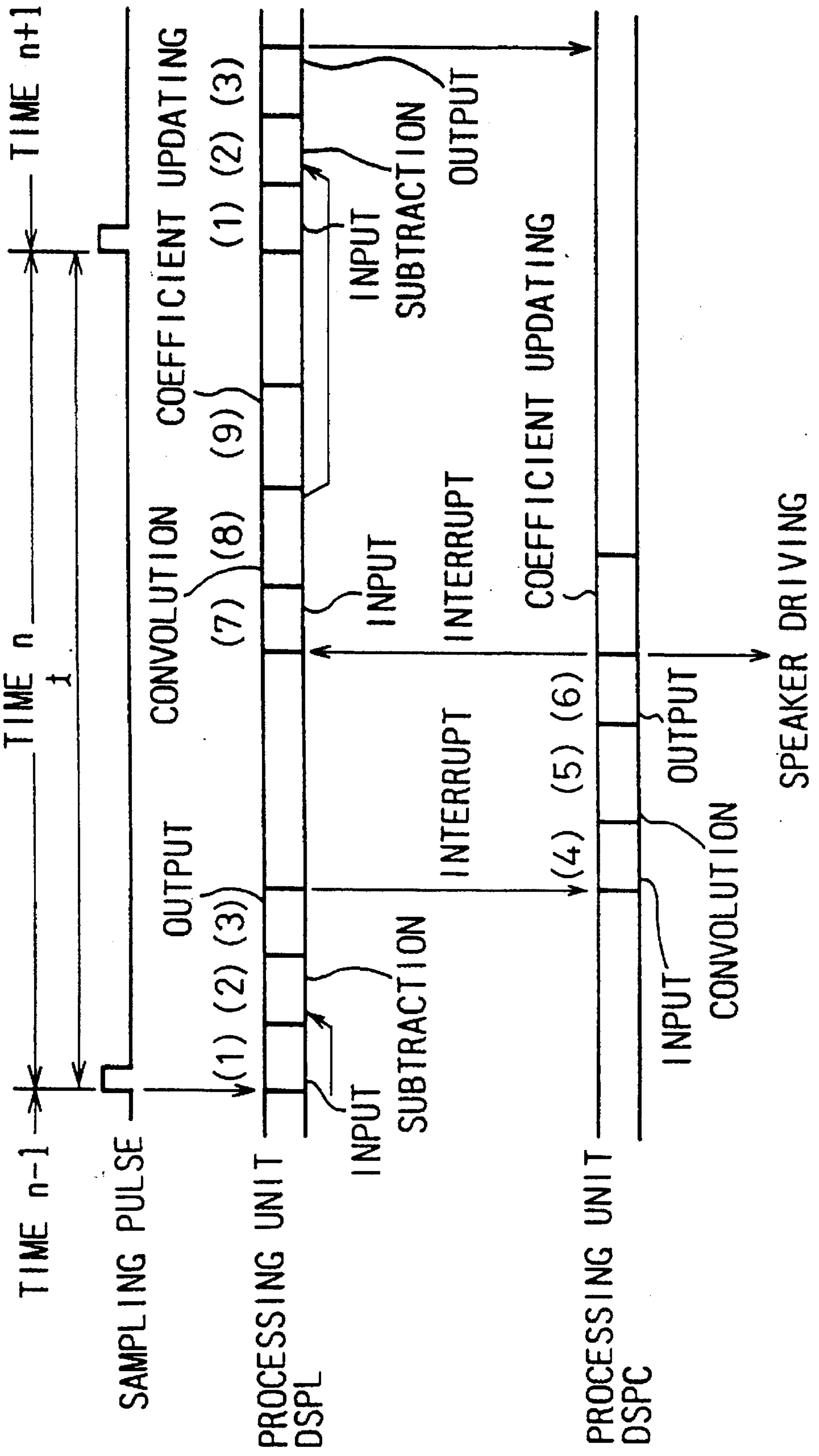
FIG. 8 is a view for explaining the operation of an embodiment of the present invention.

FIG. 8 is a diagram for explaining a predetermined communication method according to an embodiment of the present invention. It shows the operations of the two processors DSPC, DSPL and the fan noise filter CO and the detouring sound filter LO disposed in these processors, respectively.

(1) The processor DSPL starts its processing on the basis of the sampling pulse of the A/D converter ADC1 and receives as an input the noise signal from the sensor microphone 1*a* throught the A/D converter ADC1, (2) subtracts the result of the convolution calculation, which has already been executed at a previous time (n−1), from the noise signal to obtain the difference (representing the pure fan noise from which the detouring sound is removed), and (3) generates an interrupt and outputs the difference to the processor DSPC.

(4) The processor DSPC inputs the difference to the fan noise filter CO, (5) executes the convolution calculation, (6) outputs the result of the calculation through the D/A converter DAC2 to drive the speaker SO and to eliminate the fan noise, generates an interrupt, and outputs the result of the convolution calculation to the processor DSPL.

(7) The processor DSPL receives as an input the result of the convolution calculation from the processor DSPC (which represents the speaker sound) and supplies it to the detouring sound filter LO, (8) executes the convolution calculation to simulate the detouring sound, (9) updates the filter coefficient $h_i$ of the detouring sound filter LO on the basis of the difference obtained in (2) above, and waits for the sampling pulse.

When the sampling pulse is generated, the silencing control, which always takes the detouring sound into consideration, is executed by repeating the operations described above.

Figure 9:
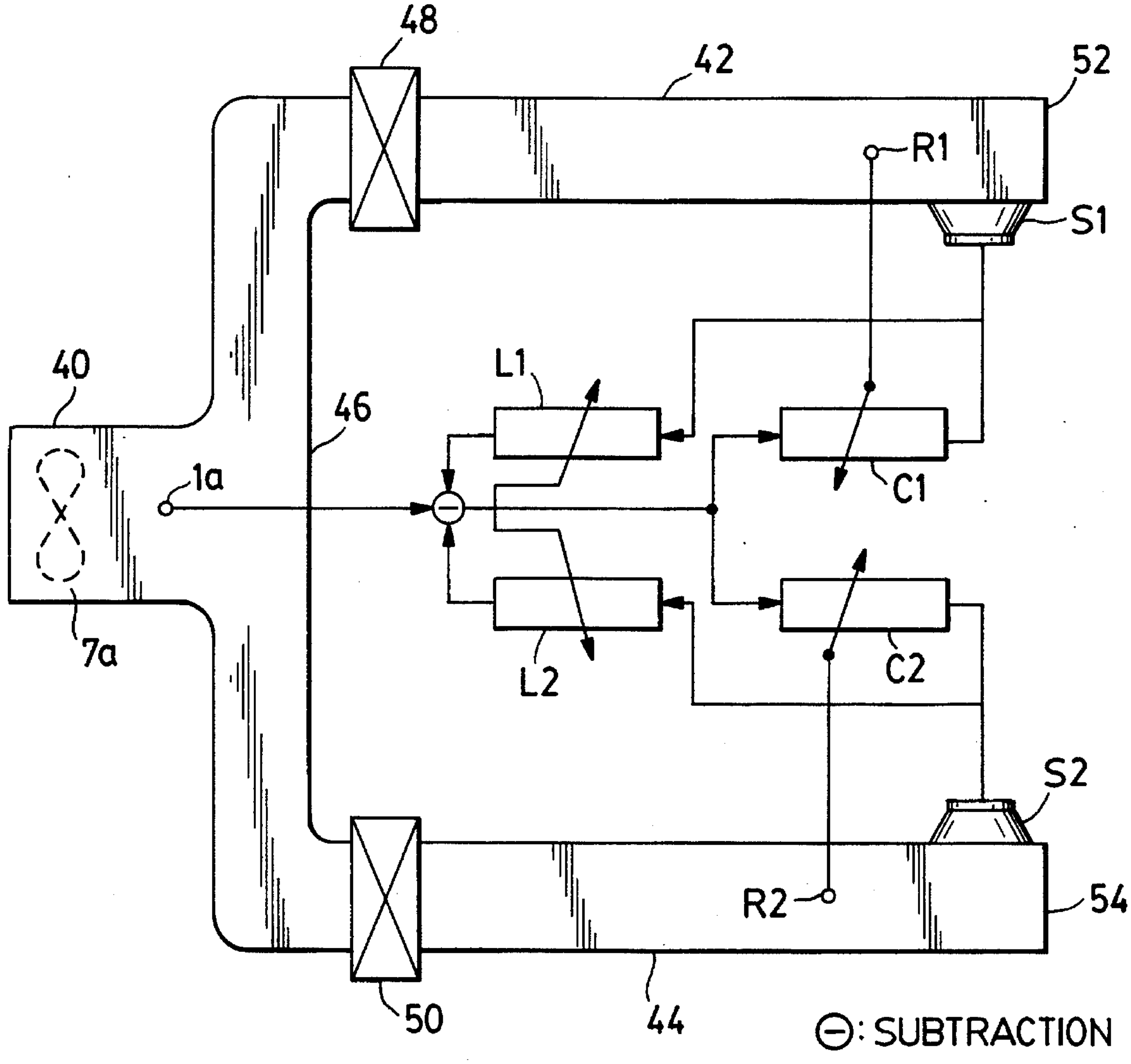
FIG. 9 is a block diagram showing a second embodiment of the present invention.

FIG. 9 is a block diagram showing the second embodiment of the present invention.

To simplify the drawing, the A/D converter and the D/A converter are omitted, and the filter coefficient control unit and the filter coefficient are represented by oblique arrow marks.

This embodiment is applied to a cooling system wherein the duct uses a single suction port (40) of cool air. This is branched into two ducts 42 and 44 from an intermediate portion 46. Each branch duct 42 and 44 respectively passes through separate heat sources 48 and 50 source and extends respective exhaust ports 52 and 54. A common fan 7*a* and a common sensor microphone 1*a* are disposed at the suction port of the duct, and speakers S1, S2 and error microphones R1, R2 are disposed at each exhaust port. The upper and lower halves of the drawing correspond to the branched ducts. The sensor microphone 1*a* receives the fan noise and the detouring sound from each speaker S1, S2 in the same way as in the first embodiment. Accordingly, a signal purely representing the fan noise from which the detouring sound is removed can be obtained by subtracting the output of the detouring sound filters L1, L2 for simulating the detouring sound transmitted through each branched duct from the sound signal received by the sensor microphone 1*a*.

This fan noise signal is input to each fan noise filter C1, C2 for simulating the behavior of the fan noise transmitted through each branched duct. Each speaker S1, S2 is driven by the output of the corresponding fan noise filter C1, C2 so as to eliminate the fan noise transmitting through each branched duct. The filter coefficient of each fan noise filter is corrected and updated on the basis of the residual noise from each error microphone R1, R2.

Though the second embodiment of the present invention represents the case of two branched ducts, the present invention can of course be applied to all numbers of branch ducts.

In the explanation made with reference to FIG. 8, two processors (DSPC, DSPL) directly generated interrupts for communication. However, it is also possible to employ a system wherein two processors generate interrupts indirectly through another processor, a system wherein two processors communicate with each other through a direct interface directly exchanging data with them, or a system wherein flags are disposed so as to represent that data to be exchanged between two processors exists and are monitored by a timer or by converting the number of steps of a program to the time to monitor the flags every predetermined time.

As described above, in the active noise elimination apparatus in a cooling system according to the present invention, the first digital filter simulates noise from the blower, the second digital filter receives as input a noise simulating signal of the first digital filter to simulate the detouring sound from the speaker, the subtraction means subtracts the detouring sound simulating signal of the second digital filter from the noise signal received by the sensor microphone, and the first digital filter effects simulation on the basis of the result. Accordingly, it becomes possible to simulate the noise purely generated from the blower by removing the detouring sound, the noise from the blower can correctly be offset and eliminated by driving the speaker on the basis of the output of the first digital filter. Since both digital filters are subjected to parallel processing by individual processors, processing can be executed within a short time, so that the duct need not be extended and a high speed processor is not required. For these reasons, the present invention can efficiently and economically eliminate the noise.

We claim:

1. An active noise control system for canceling noise, produced by a blower and propagating through a duct, at an exhaust port of the duct, comprising:

first reception means disposed within the duct for receiving noise generated by the blower and outputting a noise signal in response thereto;

sound generation means, responsive to a noise canceling signal, for generating noise canceling sound that cancels the noise generated by the blower at the exhaust port of the duct;

second reception means for receiving the noise generated by the blower and the noise canceling sound generated by the sound generation means at the exhaust port of the duct and outputting a residual error signal in response thereto;

first simulation means including a first digital signal processing unit for receiving a subtraction signal which simulates the noise produced by said blower and for outputting the noise canceling signal to said sound generation means in response thereto;

first controlling means for controlling the first simulation means to update the noise canceling signal in response to the residual error signal output by the second reception means;

second simulation means including a second digital signal processing unit different from the first processing unit for receiving the noise canceling signal output from said first simulation means and for outputting a detouring sound simulating signal which simulates the noise canceling sound produced by said sound generation means as received by said first reception means through said duct;

second controlling means for controlling the second simulation means to update the detouring sound simulating signal in response to the subtraction signal; and subtraction means for subtracting the detouring sound simulating signal output by said second simulation means from the noise signal output by said first reception means and for outputting the subtraction signal in response thereto.

2. An active noise control system according to claim 1, wherein:

said duct includes a single suction port of cool air and is branched into a plurality N of branch ducts from an intermediate part thereof, each of said branch ducts extending to a respective exhaust port by way of a separate heat source; and said first simulation means, said second simulation means, said sound generation means, and said second reception means each respectively include means respectively corresponding to each of the plurality N of said branch ducts; and said subtraction means subtracts detouring signals output by the means of said second simulation means which respectively correspond to each of the plurality N of said branch ducts from the noise signal output by said first sound reception means and outputs a result to each of the means of said first simulation means which respectively correspond to the plurality N of said branch ducts.

3. An active noise control system according to claim 1, wherein said predetermined communication means includes means for directly interrupting the second digital signal processing unit when communicating with the first digital signal processing unit.

4. An active noise control system according to claim 1, wherein said predetermined communication means includes means for communicating with the second digital signal processing unit by monitoring an existence flag of data to be communicated by the first digital signal processing unit.

5. An active noise control system for actively eliminating noise generated by a blower at an exhaust port of a duct comprising:

a first reception device disposed in proximity to said blower for receiving noise generated by said blower and a detouring sound, and outputting an analog noise signal in response thereto;

a sound generation device for generating a noise canceling sound in response to a noise canceling sound generation signal;

first conversion means for converting the analog noise signal output by said first reception device into a digital noise signal;

a first digital filter, having a first filter coefficient, for receiving a subtraction result and outputting a digital noise simulating signal simulating the noise generated by said blower in response thereto;

second conversion means for converting the digital noise simulating signal output by said first digital filter into said noise canceling sound generation signal and for outputting the noise canceling sound generation signal to said sound generation device;

a second digital filter, having a second filter coefficient, for receiving as input the digital noise simulating signal output by said first digital filter and outputting a detouring sound simulating signal in response thereto to simulate the detouring sound, wherein the detouring sound is the noise canceling sound generated from said sound generation device when received by said first sound reception device through said duct;

subtraction means for subtracting the detouring sound simulating signal output by said second digital filter from the digital noise signal output by said first conversion means and for outputting the subtraction result in response thereto;

second updating means, receiving as input the subtraction result output by said subtraction means, for updating the second filter coefficient of said second digital filter in response thereto during active noise elimination;

a second reception device disposed in proximity to said exhaust port of said duct for receiving residual noise and outputting an analog residual noise signal in response thereto;

third conversion means for converting the analog residual noise signal output by said second reception device into a digital residual noise signal; and first updating means, receiving as input the digital residual noise signal output by said third conversion means, for updating the first filter coefficient of said first digital filter in response thereto during active noise elimination.

6. An active noise control system according to claim 5, wherein the duct includes a single suction port for receiving cool air, said duct being branched into a plurality N of branch ducts from an intermediate part thereof;

each of said plurality N of branch ducts extends to a respective exhaust port by way of respective separate heat sources, said system further comprising a plurality N of first digital filters, second conversion means, sound generation devices, second sound reception devices, third conversion means, first updating means, second digital filters, and second updating means each corresponding to each of the plurality N of said branch ducts, respectively; and said subtraction means subtracts each of a plurality N of detouring sound simulating signals output respectively by said plurality N of said second digital filters from the digital noise signal output by said first conversion means and outputs a corresponding result to each of the plurality N of said first digital filters in response thereto.

7. An active noise control system according to claim 5, wherein said first digital filter and said second digital filter are comprised of respective first and second processing units, and communication between said processing units is effected by a predetermined method.

8. An active noise control system according to claim 7, further comprising means for directly interrupting the second digital signal processing unit during communication with the first digital signal processing unit.

9. An active noise control system with detouring sound apparatus according to claim 5, wherein the filter coefficient of said second digital filter is obtained by inputting a predetermined noise from a noise source to said sound generation apparatus and to said second digital filter and updating the filter coefficient by said second updating means in accordance with a predetermined algorithm so that the output of said subtraction means for the detouring sound becomes zero.

10. An active noise control system with detouring sound apparatus according to claim 9, wherein said predetermined noise is a white noise.

11. An active noise control system with detouring sound apparatus according to claim 9, wherein said predetermined algorithm is a learning determination method.

12. An active noise control system with detouring sound apparatus according to claim 9, wherein said predetermined algorithm is a least mean square method.

13. An active noise control system with detouring sound apparatus according to claim 9, wherein the filter coefficient of said first digital filter is obtained by fixing the filter coefficient of said digital filter obtained as described above, outputting a predetermined noise using a noise source in place of said blower, and updating a filter coefficient by said first updating means in accordance with a predetermined algorithm so that a residual noise signal from said second sound reception device becomes zero.

14. An active noise control system with detouring sound apparatus according to claim 13, wherein said predetermined noise is a white noise.

15. An active noise control system with detouring sound apparatus according to claim 13, wherein said predetermined algorithm is a learning determination method.

16. An active noise control system with detouring sound apparatus according to claim 13, wherein said predetermined algorithm is a least mean square method.

17. An active noise control system with detouring sound apparatus according to claim 13, wherein the filter coefficient of said second digital filter is determined only at the start of the operation of said apparatus and is fixed during the subsequent operation of apparatus, and the filer coefficient of said first digital filter is constantly updated during the operation of said apparatus.

18. An active noise control system comprising:

a sensor transducer for receiving noise and outputting an electrical noise signal in response thereto;

an error transducer for receiving error noise and outputting an electrical error noise signal in response thereto;

a first simulation processor for outputting a first simulation signal during a first predetermined period in response to a received subtraction signal;

first means for updating the first simulation processor to update the first simulation signal in response to the subtraction signal;

an output transducer electrically connected to the first simulation processor for producing an acoustic vibration in response to the first simulation signal;

a second simulation processor electrically connected in parallel with the first simulation processor and receiving the first simulation signal therefrom, for outputting a second simulation signal during a second predetermined period in response to the subtraction signal and the first simulation signal;

second means for controlling the second simulation processor to update the second simulating signal in response to the subtraction signal; and subtraction means electrically connected to and communicating with the sensor transducer for subtracting the second simulation signal from the electrical noise signal and outputting the subtraction signal in response thereto.

* * * * *

UNITED STATES PATENT AND TRADEMARK OFFICE

CERTIFICATE OF CORRECTION

PATENT NO. : 5,583,943

DATED : December 10, 1996

INVENTOR(S) : Tadashi Ohashi et al.

It is certified that error appears in the above-indentified patent and that said Letters Patent is hereby corrected as shown below:

Col. 1, line 24, insert --,-- after "noise" (second occurrence);

line 58, delete "and".

Col. 5, line 1, insert --as-- after "the".

Col. 5, line 1, insert --as-- after "noise),"

Col. 7, line 60, insert --the-- after "by".

Col. 8, line 5, change "learnt" to --learned--;

line 67, delete "source"; insert --to-- after "extends".

Col. 12, line 47, insert --said-- after "of" (first occurrence); change "filer" to --filter--.

Signed and Sealed this

Twentieth Day of May, 1997

Attest:

Bruce Lehman

BRUCE LEHMAN

*Attesting Officer*

*Commissioner of Patents and Trademarks*